United States Patent [19]

Ackermann, Jr. et al.

[11] Patent Number: 4,766,647
[45] Date of Patent: Aug. 30, 1988

[54] APPARATUS AND METHOD FOR MEASURING A PROPERTY OF A CONTINUOUS STRAND OF FIBROUS MATERIALS

[75] Inventors: Norbert J. Ackermann, Jr.; Hossein M. Ghorashi; Peyman H. Dehkordi, all of Knoxville, Tenn.

[73] Assignee: Spinlab Partners, Ltd., Richmond, Va.

[21] Appl. No.: 36,999

[22] Filed: Apr. 10, 1987

[51] Int. Cl.$^4$ .................... G01N 19/08; D01H 5/38
[52] U.S. Cl. ........................... 19/0.22; 19/240; 73/160; 73/703
[58] Field of Search .................. 19/22, 239, 240; 73/703, 160

[56] References Cited

U.S. PATENT DOCUMENTS

| | | | |
|---|---|---|---|
| 2,981,986 | 5/1961 | Neil | 19/240 |
| 3,185,924 | 5/1965 | Locher | 324/61 P |
| 3,710,421 | 1/1973 | Tooka | 19/240 |
| 3,822,590 | 7/1974 | Tharpe et al. | 19/240 X |
| 3,854,330 | 12/1974 | Wildbolz | 73/160 |
| 3,916,687 | 11/1975 | Loepfe et al. | 19/239 |
| 3,925,850 | 12/1975 | Lytton | 19/98 |
| 3,984,895 | 10/1976 | Grice, Jr. | 19/240 |
| 4,045,659 | 12/1977 | Akagawa et al. | 73/160 |
| 4,133,207 | 1/1979 | Weidmann et al. | 73/160 |
| 4,199,844 | 4/1980 | Goetzinger | 19/240 |
| 4,473,924 | 10/1984 | Hartmannsgruber et al. | 19/240 X |

FOREIGN PATENT DOCUMENTS

| | | |
|---|---|---|
| 3237357 | 7/1983 | Fed. Rep. of Germany . |
| 509569 | 8/1971 | Switzerland . |
| 515487 | 12/1971 | Switzerland . |
| 543075 | 11/1973 | Switzerland . |

Primary Examiner—Louis K. Rimrodt
Attorney, Agent, or Firm—Staas & Halsey

[57] ABSTRACT

A method and apparatus are disclosed primarily for measuring the linear density of a sliver of fibrous strands (e.g. textile) as they are drawn through a trumpet on a processing machine. The measurement is made by detecting the naturally occurring acoustic emissions or signals generated by the frictional and compressive forces between the fibers and between the fibers and the wall of the trumpet as the sliver is drawn through the trumpet. The intensity of the acoustically emitted signal is proportional to the density of the sliver passing through the trumpet. These acoustic emissions are detected by a microphone which convert the acoustic signals to an electronic signal which is amplified and electronically processed to indicate the density of the sliver and may be used to control the textile machine and furnish diagnostic data.

15 Claims, 4 Drawing Sheets

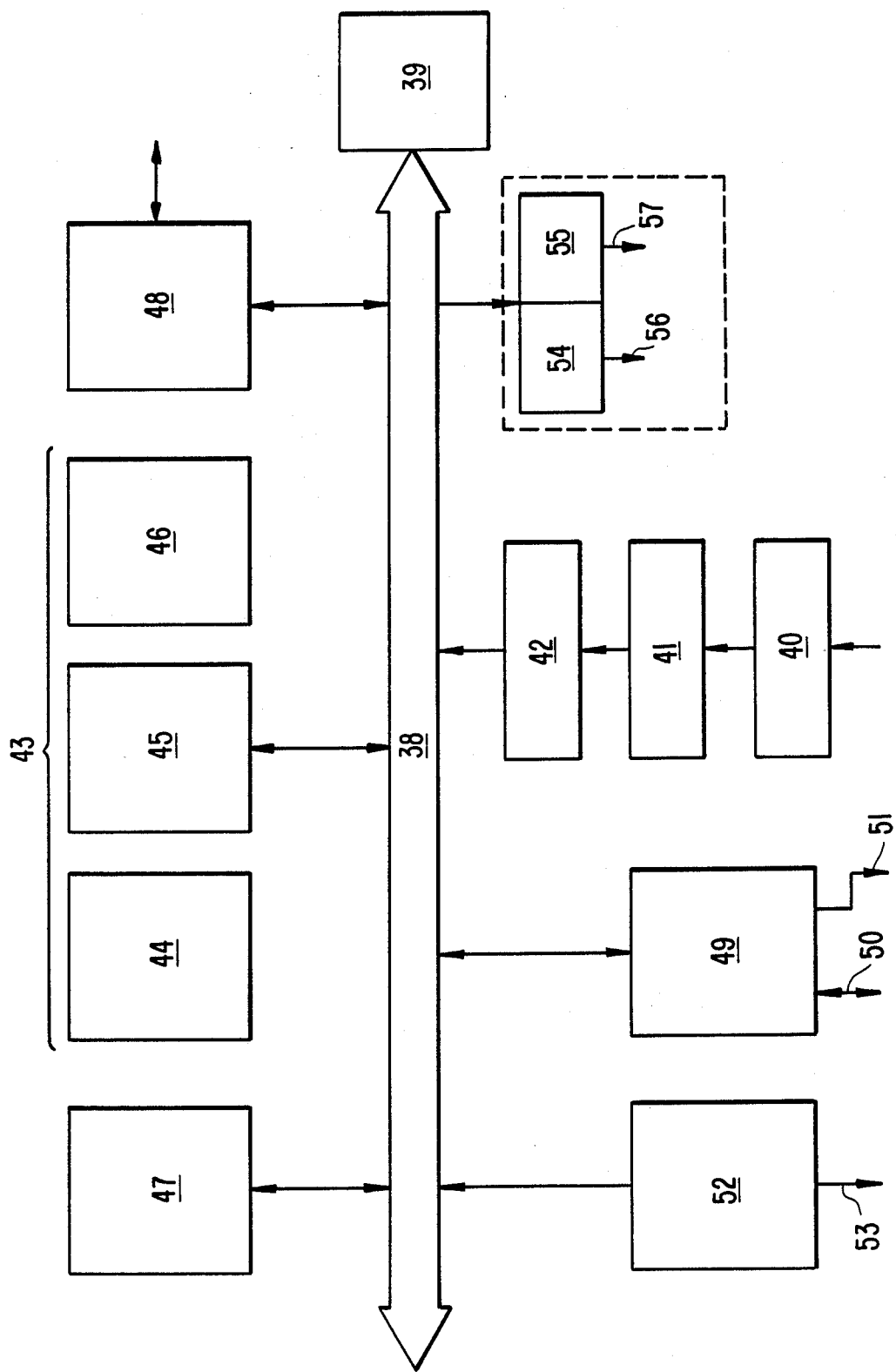

APPARATUS AND METHOD FOR MEASURING A PROPERTY OF A CONTINUOUS STRAND OF FIBROUS MATERIALS

This invention relates to the measurement of the linear density of a continuous strand of fibrous material.

The variation of weight per unit length, or linear density, sometimes referred to as an evenness, is one of the most important properties or characteristics of a fibrous strand especially for textiles. It is a fundamental property upon which other properties such as strength and appearance are directly dependent or by which they are greatly influenced. Since most of the irregularity of strand density originates in the early stages of manufacture and is carried forward and often times amplified by each stage through spinning; it is desirable to correct product variation at or near the point of occurrence such as during the carding, combing or drawing stages. As used herein, textile strands can be slivers, tow, roving and yarn produced from stable fibers.

Numerous efforts have been made in the past to measure linear density using as example techniques such as capacitance sensing, volume sensing, pneumatic sensing of pressure differences, and the damping/delaying of pulsed acoustical signals. Some of these techniques have found commercial use but all need improvement as to accuracy and/or reliability and/or space utilization and sensor access.

The purpose of this invention is to introduce a new technique for quality control in the textile industry and other fibrous strand production operations. Textile mills receive raw cotton and ship finished fabrics. An important intermediary is sliver, a soft "rope" of partially aligned fibers of up to several centimeters in diameter. The invention provides a means for the continuous and automatic inspection of sliver during the carding/drawing/blending operations whereby it is refined on it way to becoming yarn. By way of example, the invention may be utilized with a drawframe which blends sliver at a nominal 1700 feet per minute (28.3 feet per second) through a drawing station. At the drawing station, eight input slivers pass at about 4 feet per second onto rollers which draw the material out in an 8:1 ratio, also flattening the slivers to produce a sheet of aligned fibers travelling at high velocity. This material passes through a brass guide and into a "trumpet". The trumpet is usually made of a ferrous metal such as cast iron. By passage through the trumpet it is reconstituted as a single sliver, which is pulled through by rollers below and collected in a bin. This operation is used to blend dissimilar materials (cotton and synthetic fibers), and to improve the alignment of the fibers conferring strength on the end product. In normal production, this blending operation is carried out two or three times before the sliver is spun into yarn.

The present invention monitors the naturally occurring acoustic signal generated by frictional processes as the sliver is drawn through the trumpet. Here the sliver is compressed to typically 3.5 mm diameter (in the free state it is about 10 mm diameter) as it is travelling at full speed. The magnitude of the acoustic signals detected by a transducer or sensor mounted on the trumpet indicates the linear density, such as grains per yard, of the sliver. This is of major importance as stated earlier since variations in sliver linear density show up later as variations in yarn strength or appearance as blemishes in fabric appearance.

Both long term and short term variations in the linear density are indicated. Accidental breakage or loss of one of the input slivers is one case of a transient, short term variation readily detected by acoustic monitoring at the trumpet. Use of acoustic monitoring gives the operator an immediate warning of this condition. The textile machine can be arranged such that the warning signal causes an immediate shut down automatically. This could occur for reasons such as material becoming wrapped around a roller or jamming in the trumpet. In such cases the operator cleans up and rejoins the slivers by hand then switches the machine on again. Interruptions of this kind create irregularities in the output sliver, and the monitor wil detect the impact of these irregularities on the end product by acoustic monitoring of later blending operations.

Periodic short-term variations adversely affecting product quality, can be caused by various machine conditions such as misaligned or damaged rollers. The periodicity corresponds to the roller's rotational frequency, and this is the basis of important and well known diagnostic techniques used in existing machines which use sensing techniques different from the present invention, such as capitance sensing, for sensing sliver linear density and calculating spectrograms as well as continuous measurements. The naturally occurring acoustic sensing used in the present invention is utilized in a similar manner for diagnostics and production of spectrograms in addition to its principle purpose of on-line continuous linear density measurement. The spectrograms show frequency or wave lengths on the horizontal or main ordinate and amplitude on the vertical or other ordinate.

In addition to being used for monitoring, the signal giving sliver linear density can be used for regulation with an auto-levelling device. This represents the fullest use of such a device providing the ability to produce sliver of the highest evenness.

The present invention significantly improves both operating cost control and fabric quality in the textile industry by providing a continuous on-line measurement of sliver evenness or linear density. It does this by measuring naturally occurring acoustic emissions which result from the forces generated by the compressive and frictional stress waves caused when the sliver is forced through the narrow opening of the trumpets. These waves are the result of the friction between the fibers in the sliver and between the fibers and inside wall of the trumpet. The emissions are typically in the range of 1 to 1,000 kiloHertz (40 to 120 kHz for particular machine) and are detected by an acoustic sensor coupled with the trumpet as a sliver passes through the trumpet at, as one example, approximately 1,700 feet per minute. The intensity of the acoustically emitted signal properly conditioned is proportional to the linear density of the sliver passing through the trumpet. In addition to the sensor, there is an in-line pre-amplifier and a local monitor which includes signal processing and a control unit. Up to eight sensors can be serviced by each local monitor, and all of the local monitors feed into a single central analyzer. The sensor is a miniaturized, high sensitivity microphone typically 0.25 inches in diameter by 0.375 inches long having a peak frequency response generally in the range of between 1 to 1,000 kiloHertz but chosen for a narrower range tuned for each particular machine e.g. between 60 and 120 kiloHertz for a particular drawframe. It is attached to the trumpet by readily available acoustic coupling grease or adhesive such as a cyanoacrylate. The trumpet mounting may be modified to help isolate contaminating noise generated by the textile machinery from the acoustically emitted signal caused by the sliver passing through the trumpet. The modification is done to avoid metal-to-metal contact (i.e. signal transmission paths) between the trumpet and its support. For example, a rubber ring can be inserted between the trumpet and its support plate and nylon screws used to attach the trumpet to the plate. Additionally, frequencies between 40 kiloHertz are filtered out, but this can vary with different machines. This helps reduce interference from background machine noise.

The method and apparatus will now be described in more detail with reference to the following detailed description and the accompanying drawings, wherein:

FIG. 6 shows a block diagram of the local monitor.

Figure 1:
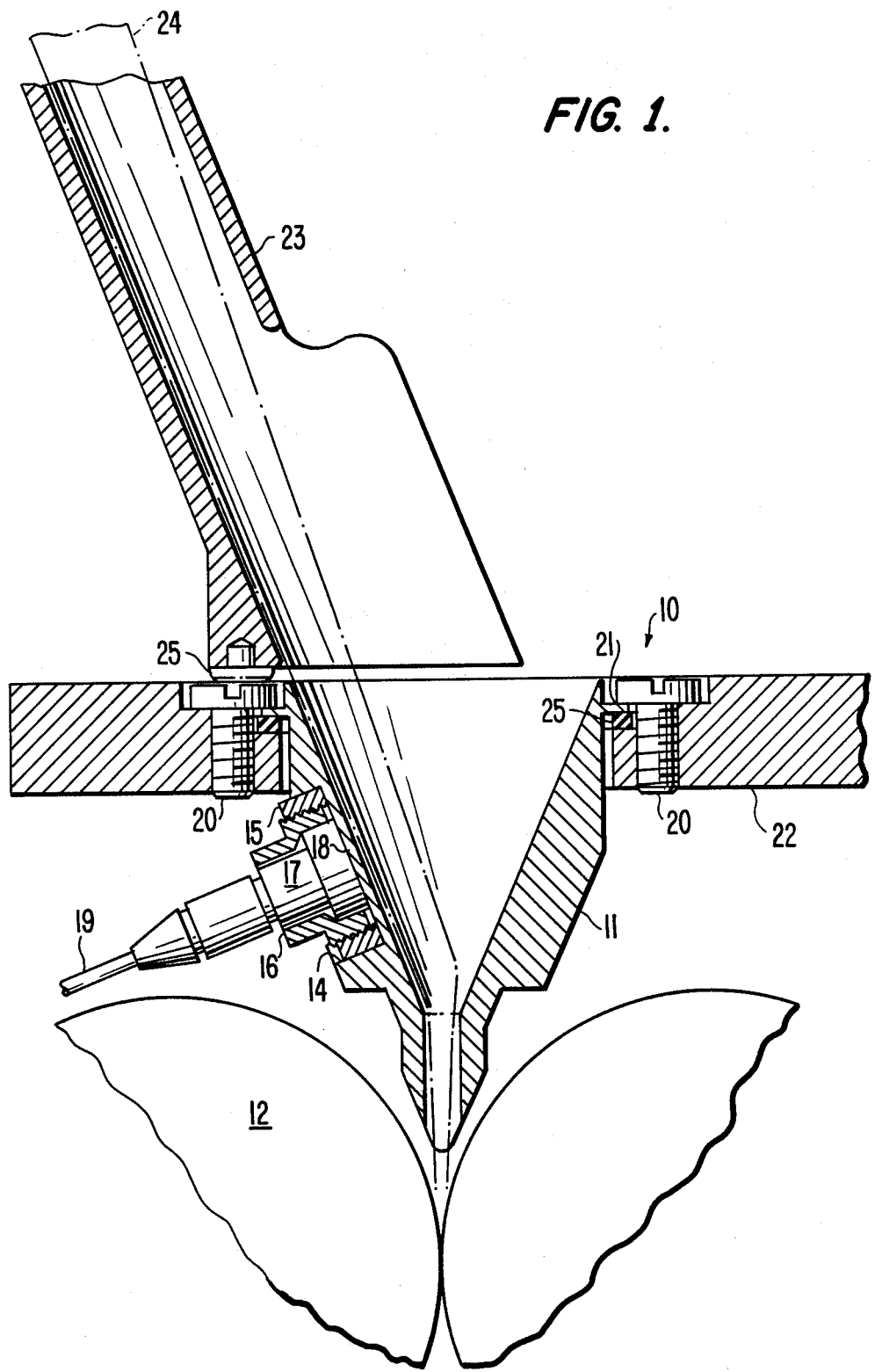
FIG. 1 shows a section view of the sensor and trumpet of the invention assembled together and located in the nip of two calendar rolls.

With reference to FIG. 1, there is shown a section view of a portion of a drawing machine 10 having a trumpet 11 located in the nip formed between rear calendar roll 12 and front calendar roll 13. A circular portion 14 is cut out of the side wall of the trumpet into which is press fitted a retainer ring 15. The sensor 17 is a highly sensitive miniaturized microphone 0.25 inches in diameter by 0.375 inches long. The microphone has a peak frequency response tuned for a particular machine between 60 and 120 kiloHertz and is available from the Physical Acoustic Corporation at Post Office Box 3135, Princeton, NJ 08540 U.S.A. as No. S9224 High Frequency Acoustic Sensor (miniaturized). The sensor 17 is joined to the sidewall of the trumpet at the bottom of the cutout portion 14 by means of an acoustic coupling grease or adhesive commonly available such as cyanoacrylate. To assist in holding the sensor to the sidewall of the trumpet by mechanical means is a threaded sensor holder 16 which threads into the internal threads of retainer ring 15. The sensor or transducer 17 is connected to the electronics of the system by means of cable 19.

The trumpet is held in the drawing machine of FIG. 1 by means of two nylon screws 20 which clamp the flange 21 of a trumpet to the trumpet bracket 22. A sliver condenser 23 guides a sliver 24 into the mouth of the trumpet which condenses the slivers and compresses them as they go through the trumpet and converge to exit through the small orifice at the bottom of the trumpet as shown in FIG. 1. It is important that the trumpet is mounted in the textile machine in a constant mechanical alignment relative to the sliver travel and this can vary from machine to machine. With further reference to FIG. 1, the trumpet should be at least partially acoustically isolated from the textile machine so as to reduce interference from background machine noises. This is accomplished in FIG. 1 by means of rubber insulator 28 being inserted between the trumpet 11 and the trumpet bracket 22 and between the condenser 23 and the trumpet 11.

Figure 2:
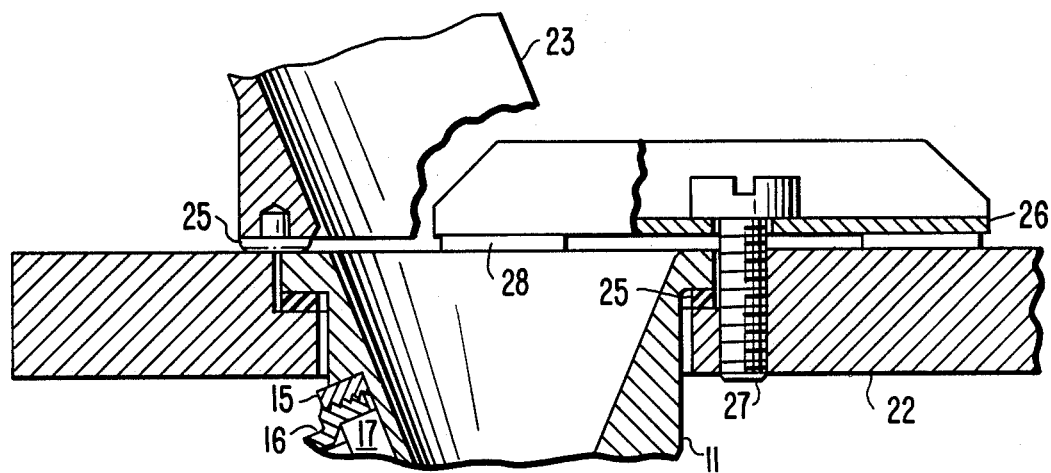
FIG. 2 shows a broken away section similar to FIG. 1 wherein the trumpet is alternatively held in place by retainer rather than by screw heads.

FIG. 2 shows a modification of the mounting of the trumpet from FIG. 1. In FIG. 2, the trumpet 11 is held to the trumpet bracket 22 by a trumpet retainer 26 attached to the trumpet bracket by means of retainer screw 27. Again, acoustical isolation of a trumpet from the textile machine is desirable and provided for by rubber insulators 25 between the trumpet and the trumpet bracket and between the sliver condenser and the trumpet. Additionally, rubber isolator 25 is placed between the trumpet retainer and the trumpet and trumpet bracket.

Figure 3:
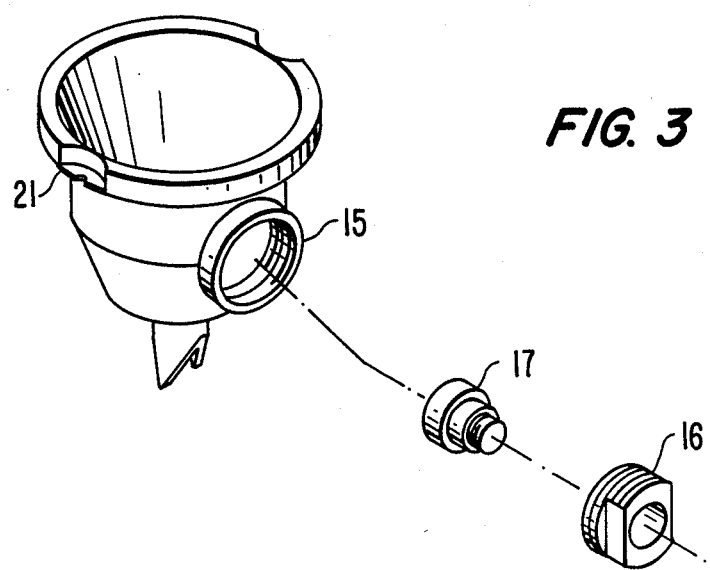
FIG. 3 shows a perspective exploded view of the sensor and trumpet sub-assembly.

FIG. 3 is an exploded view in perspective of the sensor and the trumpet subassembly. It shows the trumpet 11 utilized in FIG. 1 which has flanges 21 to accomodate the nylon screws and a sensor retaining ring 15 which has been press fitted into the trumpet cut out portion 14. The retaining ring has internal threads to accomodate the external threads of sensor holder 16 which mechanically holds sensor 17 adjacent to the sidewall of the funnel when assembled. As best seen in FIG. 1, the sensor holder 16 has a bore which is enlarged at one end to accomodate the enlarged head of the sensor 17 so as to mechanically hold it adjacent the sidewall of the trumpet to augment the acoustic coupling adhesive 18.

Figure 4:
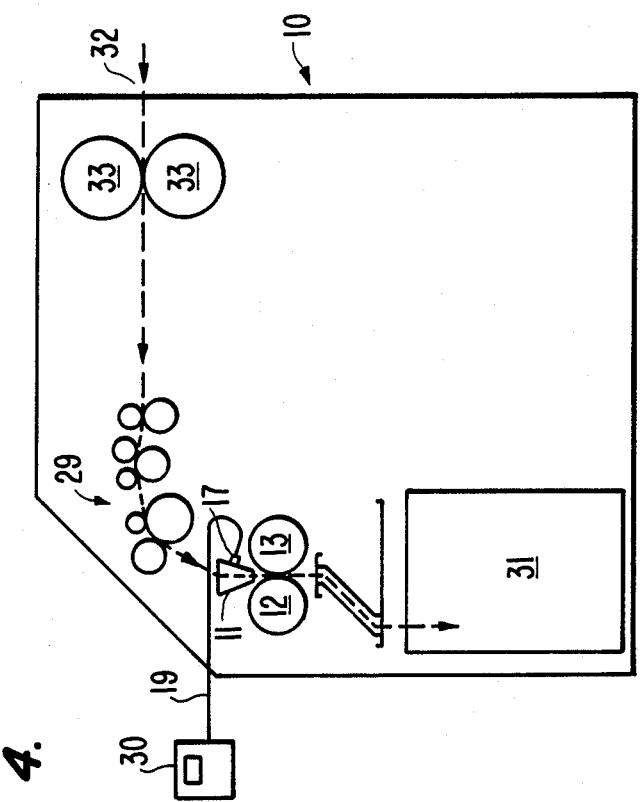
FIG. 4 shows a schematic of a drawframe with the sliver monitor in position.

With reference to FIG. 4, there is shown a schematic of textile machine such as a drawframe or drawing machine 10 which has a drafting element 29 upstream from the trumpet 11 with its sensor 17 connected to a sliver monitor recorder 30 by means of cable 19. Downstream from the trumpet are two calendar rolls 12 and 13 which draw the sliver through the trumpet and inject it through a pathway into bin 31. The sliver pathway 32 starts it from the right in FIG. 4 where the sliver passes through two rolls 33, then through drafting element 29 and then through sliver condenser (not shown in FIG. 4) into the large opening of the funnel or trumpet which converges in the direction the sliver is moving. The sliver is compressed down into a smaller diameter before passing to calendar rolls 12 and 13 into the bin 31. The on-line continuous sensing by means of sensor 17 is recorded, as shown schematically by sliver monitor recorder.

Figure 5:
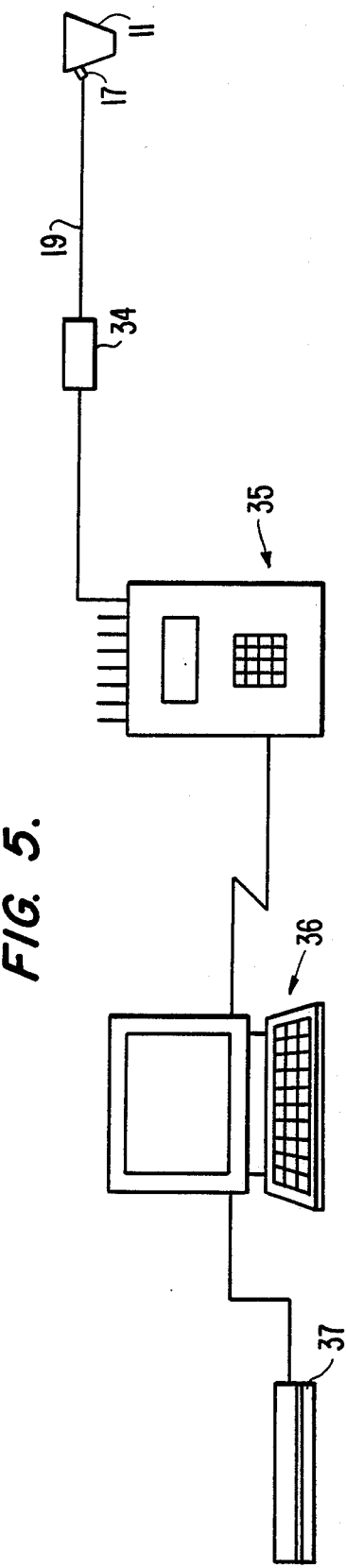
FIG. 5 shows the major elements of a sliver monitor system.

With reference to FIG. 5, there is shown the major elements of the sliver monitor system. Beginning with the trumpet 11, sensor 17 and cable 19, the cable feeds the signal transduced from acoustical to electrical by the sensor 17 to the preamplifier 34 where the signal is amplified and transmitted to local monitor 35. The local monitor provides power to the preamps and receives their signals. The monitor shown can handle from one to eight channels providing further signal amplifications and bandpass filtering, provide a conversion of the signal to a root means squared (RMS) voltage output, and typically a one millisecond time averaging in each channel. These channel feed into an eight channel multiplexer, anti-aliasing filter with gain and a 30 kiloHertz 12 bit single channel analog to digitial (A/D) transducer. The A/D feeds a microprocessor where any desired mathematical and logical functions are performed. The local monitor also includes a 24 bit parallel port, two serial ports, a keypad and liquid crystal display.

The local monitor operates in two modes, surveillance and diagnostic. While in the surveillance mode, the local monitor continuously collects the data from the eight input channels computing the sliver count (usually grains per yard and a typical value in one operation is 58.5 grands/yd) and the CV % (The coefficient of variation or unevenness. It is the standard deviation of the linear densities over which unevenness is measured expressed as a percentage of the average linear density for the total length with which unevenness is measured). The local monitor also provides a local digital output for control usage. The sliver count and the CV % are continuously compared against set points for limits by the local monitor which limits are selectable by the operator. If either the sliver count or CV % are found to be outside the set points for the limits, a local signal is provided which may set off an alarm and/or shut the textile machine down. Also the local monitor passes all this information to a central analyzer 36 for a comparable and more extensive analysis.

Also, the sliver count signal can be provided to a regulation system to provide a control system.

When in the diagnostic mode, the local monitor isolates temporarily the focus onto a single channel for more comprehensive data collection and passage to the central analyzer.

The local monitor can also receive information, in addition to the acoustic data, about the machine operation through a 24 bit parallel port for processing to the central analyzer (e.g., machine running status, operational downtime modes, etc.) from the remainder of the drawframe regular control system (not shown).

The local monitor has a keyboard and liquid crystal display for local interaction. The operator can request and receive at any time the sliver count and CV % for any channel of the local monitor.

The central analyzer 36 is a commonly available 16 bit based personal microcomputer (e.g., IBM PCXT model manufactured by International Business Machines Armonk, NY, U.S.A. with ports for communication to the local monitors and for communication to the factory's host computer. The central analyzer includes a generally available software based Fast Fourier Transform (FFT) program or a generally available fast Fourier transformer processor board. It also has a color graphic controller, a 10 megabyte hard disc and is connected with the usual peripherals such as a printer 37. These components are all readily available and will be obvious as to the selection and use by one skilled in the art.

The central analyzer performs data collection from the local monitors, data analysis and archiving and all report generations. It also performs the Fast Fourier Transform analysis in the diagnostics mode for generating the well known diagnostic spectrograms. A single central analyzer would normally be able to handle all the local monitors in a single plant.

The diagnostic techniques and the generation of the spectrogram have been well-developed with other sensing technology than that utilized by the invention disclosed herein. For example, reference is made to article entitled *Spinning Faults and the Spectrogram* by H. Locher in the January and February, 1959 issue of *MAN-MADE* Textiles published by the Buxton Press, South Avenue, Buxton, England, which were based on a paper presented at a meeting of the British Association for Quality Control (Textiles). The diagnostic principle is based on a frequency or wavelength spectrum of the sliver linear density signal. Machine failure modes are identifiable with particular characteristics of this system.

The wavelength of the fault can be represented by a simple formula which can in turn indicate the most likely source of the faults. The spectrogram usually varies from 0.1 Hertz to 500 Hertz and the amplitude can be shown as a number or converts to CV %. The benefits of quality control using such diagnostic techniques is early detection of malfunctioning machinery, and a pin-pointing of the machinery problems, in addition to large reduction in off-quality sliver, CV % monitoring, and production monitoring. The diagnostic technique is essentially the same as that used by other sensing technologies, the difference being in the use of the special naturally occurring acoustical emitted signal of this invention.

Reference is now made to FIG. 6 wherein shown a block diagram of the local monitor 35 of this invention which has already been described. Shown in the diagram are the system bus 38 for bussing the data, control and address information with an expansion connector 39 at one end. The incoming analog signals from the preamplifier which may be up to eight in number, are introduced into the analog multiplexer 40 which feeds into the high and low pass filter and amplifier 41. The high and low pass filter frequencies are chosen for the particular characteristics of the machine being monitored but can generally range from 1 to 1,000 kiloHertz. For a particular machine these were chosen to filter out signals below 40 kiloHertz and above 180 kiloHertz where most of the interferring noise generated by the environment, especially machine noise, is found. While the filter is appropriate for the drawing machines used, it can be chosen for a different frequency for different machines if such appears to be appropriate. The signal is also root-mean-squared (RMS) and time averaged with a time constant typically of 1 milisecond. The signal is then fed into a 12-bit A/D converter 41 and then into the system bus. The local monitor also has sufficient memory 43 for its functions with separate storage for data 44 (32k RAMS) and 46 (2k EEPROMS). It also provides program storage 45 made up of 24k (EEPROMS). A standard microcontroller 47 performs local control functions and the parallel input/output (I/O) 48 has accomodations for 20 lines. The output from the system bus is through RS 232 and RS 422 ports 49 using transistor-transistor logic (TTL) and feed to a host computer 50 and display 51.

The local monitor also has a keyboard interface 52 (4×5 matrix) feeding to the keyboard 53). For optional future expansion, the local monitor has expansion capability of two digital to analog converters (DAC) 54 and 55 feeding to a first analog output 56 and a second analog output 57.

In calibrating the monitor, one example is to obtain a first reading with a normal sliver made of eight individual slivers being drawn through the frame. Then one of the input slivers is removed and the seven remaining slivers are drawn through the frame and a second reading is taken. This is an approximately 12% variation and is utilized in calibrating the instrument. Of course, other similar techniques can be used.

In practice, generally a variation from normal greater than 5% is sufficient for most operators to stop the textile machines and correct any fault creating such a wide variation. Generally, it is desirable to be able to control to a variation of 1% but 2.7% embraces a standard range. These variations are well within the capability of the present technique which is so satisfactory that on-line monitoring is comparable to or better than the standard quality inspection made off-line.

The basic invention presents a new technology for sensing linear density variations in a fibrous textile strand on-line as it passed through a trumpet-like device used in textile machinery. The detection and utilization of the naturally occurring acoustic emissions as a signal give rise to the other numerous benefits resulting from this new technique including the diagnostics, control, alarm and other functions.

While it is found preferable to have the acoustic pick-up device or sensor as used in the invention directly coupled to the wall of a standard like trumpet of trumpet-like device, other acoustical couplings are possible (e.g., using waveguides, etc.).

Many other features and advantages of the present invention are apparent from the detailed specification, and thus, it is intended by the appended claims to cover all such features and advantages which fall within the spirit and scope of this invention. Further, since numerous modifications and changes will readily occur to those skilled in the art, from the disclosure of the invention, it is not desired to limit the invention to the exact construction and operation illustrated and described. For example, while a slightly modified standard trumpet already present on a textile machine is utilized in practicing the invention, other trumpet-like devices could be used for compressing the fibers together and generating the naturally occurring acoustic emission as the fibrous strand passes through the device. Accordingly, suitable modifications and equivalents may be resorted to, all falling within the scope and spirit of the invention.

Also, while the particular application filed cited is for textile, it is intended that the invention be used for any continuous strand of fibrous material.

What is claimed is:

1. A monitor for sensing the varying linear density along the length of a moving fibrous strand comprising:
   a trumpet-line device having a throughput opening with an inside surface with which said strand frictionally engages as it passes through said opening in a compressed state;
   a high frequency acoustical to electrical transducer coupled acoustically to said trumpet-like device for detecting the naturally occurring acoustically emitted signals generated by the friction between the fibers of said strand and between said strand and said inside surface of said trumpet as the strand passes in a compressed state through said trumpet, said transducer converting said acoustically emitted signals to an electrical signal which varies with the intensity of said acoustically emitted signals and which variation is proportional to the density of said fibrous strand; and
   an electronic apparatus for receiving said varying electrical signal and indicating the variations in intensity of said emitted signal and thereby variations in density along the length of said fibrous strand.

2. The monitor of claim 1 wherein the said transducer is a miniaturized microphone having a peak frequency response between typically 60 and 120 kiloHertz (chosen according to the characteristics of the monitored machine).

3. The monitor of claim 1 wherein said microphone is attached to the outside wall of said trumpet-line device by an acoustic coupling grease or adhesive.

4. The monitor of claim 2 wherein said microphone is mechanically held in close acoustical coupling to the outside wall of said trumpet-like device by a mechanical retaining means.

5. The monitor of claim 1 wherein said electrical signal is filtered to eliminate frequencies typically between 40 kiloHertz and above 180 kiloHertz (chosen according to the particular characteristics of the monitored machine).

6. The monitor of claim 1 wherein the signal is converted to a root-means-square (RMS) voltage output and averaged with a one millisecond time average.

7. A method for measuring the varying density along the length of a fibrous strand comprising the following steps:
   draw said fibrous strand through a trumpet-like funnel which compresses the diameter of the strand;
   measure by an acoustical electrical transducer the intensity of the naturally occurring acoustical emissions generated by the friction between the fibers in said compressed strand and between said compressed strand and said funnel; and
   indicate said measurement of said intensity in a useable form.

8. The method of claim 1 wherein the electrical signal results from said transducer is filtered of frequencies typically below 40 kiloHertz and above 180 kiloHertz (chosen according to the particular characteristics of the monitored machine).

9. The method of claim 7 wherein the signal is converted to a root-means-square (RMS) voltage output and averaged with a one millisecond time average.

10. A textile machine for processing a sliver comprising:
    apparatus for processing said sliver;
    opposed rolls for pulling said sliver;
    a trumpet located adjacent the entrance to said opposed rolls, said trumpet of funnel-like shape having a throughput opening converging in the direction of flow of said sliver;
    a high frequency microphone attached to the outside wall of said funnel and adapted to detect the naturally occurring acoustical emissions generated by the friction between the fibers in said sliver and the friction between said sliver and the inside wall of said throughput opening in said trumpet caused when the sliver is compressed and drawn through said trumpet; and
    a device for indicating the variations in linear density of said sliver along its length based on the intensity of the said acoustical emissions detected by said microphone.

11. A textile machine of claim 1 wherein there is further provided:
    a funnel bracket attached to said textile machine to which said funnel is attached; and
    an acoustical insulator located between said bracket and said funnel to at least partially isolate said funnel from acoustical noises generated by said textile machine.

12. A monitor for sensing the varying linear density along the length of a moving fibrous strand comprising:
    a sliver funnel having a throughput opening converging in the direction of flow of the fibrous strand;
    said funnel having a side wall;

a high frequency miniaturized microphone having a peak frequency response including the range typically between 60 and 120 kiloHertz (chosen according to the particular characteristics of the monitored machine) attached to said side wall; and a means for acoustically coupling said microphone to said sidewall.

13. The monitor of claim 12 wherein said acoustical coupling is provided by an adhesive.

14. The monitor of claim 13 wherein said attachment includes a sensor holder for mechanically holding said microphone to said sidewall.

15. The monitor of claim 14 wherein said sensor holder has external threads and includes a sensor internally threaded retaining ring press fitted into a blind boring in said sidewall with said sensor holder being threaded into said retaining ring.

* * * * *